(12) United States Patent
Berry

(10) Patent No.: US 12,257,161 B2
(45) Date of Patent: Mar. 25, 2025

(54) INTERBODY DEVICE WITH ROTATING BLADE

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 0 days.

(21) Appl. No.: 18/088,842

(22) Filed: Dec. 27, 2022

(65) Prior Publication Data

US 2024/0207065 A1  Jun. 27, 2024

(51) Int. Cl.
*A61F 2/44* (2006.01)
*A61F 2/30* (2006.01)

(52) U.S. Cl.
CPC .... *A61F 2/447* (2013.01); *A61F 2002/30224* (2013.01); *A61F 2002/30433* (2013.01); *A61F 2002/30518* (2013.01)

(58) Field of Classification Search
CPC ...... A61F 2/4455; A61F 2/4465; A61F 2/446; A61F 2/447
See application file for complete search history.

(56) References Cited

U.S. PATENT DOCUMENTS

| | | | | |
|---|---|---|---|---|
| 8,292,958 | B1 * | 10/2012 | Bruffey | A61F 2/4611 606/247 |
| 9,566,165 | B2 * | 2/2017 | Lee | A61F 2/30749 |
| 9,597,196 | B2 * | 3/2017 | Janowski | A61F 2/4425 |
| 10,137,005 | B2 * | 11/2018 | Ashleigh | A61F 2/4611 |
| 10,342,674 | B2 * | 7/2019 | Bruffey | A61F 2/442 |
| 10,478,310 | B2 * | 11/2019 | Ameil | A61F 2/4455 |
| 2003/0187436 | A1 * | 10/2003 | Bolger | A61B 17/7077 606/279 |
| 2009/0105732 | A1 * | 4/2009 | Yurek | A61F 2/4611 606/151 |
| 2016/0074172 | A1 * | 3/2016 | Lee | A61F 2/442 623/17.16 |
| 2016/0374831 | A1 * | 12/2016 | Duffield | A61F 2/447 623/17.16 |

* cited by examiner

*Primary Examiner* — Ellen C Hammond
*Assistant Examiner* — Holly Joanna Lane
(74) *Attorney, Agent, or Firm* — McCarter & English, LLP; James M. Smedley; Alex Korona

(57) ABSTRACT

An interbody fusion device with an internal rotating blade is presented. The interbody fusion device has two blades which sit fully within the central cavity of the interbody device during insertion of the device. Once inserted, the blades are rotated outward from the interbody device and into the vertebral bodies in order to secure the device to the spine.

19 Claims, 7 Drawing Sheets

INTERBODY DEVICE WITH ROTATING BLADE

TECHNICAL FIELD

The present disclosure generally relates to interbody devices, and more particularly to interbody spinal fusion devices with rotating blades.

BACKGROUND

Interbody fusion devices have been around for decades with relative success. However, the device itself is typically merely a spacer to maintain a desired distance between two vertebrae. As such, supplemental fixation like screws and rods, or plate and screws, are required to provide complete fixation of the bones. More recently, screws or nails have been added to the interbody fusion devices in order to better fixate the bones, or at least prevent any migration of the device. However, both screws and nails present an additional dilemma as they must be inserted at an angle to the interbody device in order to both go through the device and penetrate into the vertebral bodies above and below. As such, the wound required for implantation needs to be larger in order to accommodate the trajectory to the screws of nails. There are also devices which feature a blade that rotates about the central axis of the inserter, the blades being captured within the central cavity of the interbody device. However, the size of these blades are constrained by the height and width of the device can only extend a limited amount. Accordingly, what is needed is a device that overcomes the shortcomings of such prior art devices.

SUMMARY OF THE INVENTION

An interbody spinal fusion method and device is provided. The interbody spinal fusion device may include a main body with a central cavity that extends from a superior to an inferior portion of the main body. The invention may further include a mounting blade strut located within the central cavity and spanning from an anterior to a posterior face of the central cavity.

The mounting blade strut has a superior and an inferior face and are at an angle to the superior and the inferior faces of the main body. The angle between the mounting blade strut and the main body may be between one and 89 degrees. The mounting blade strut has at least one blade attachment portal that runs perpendicular to the face of mounting blade strut. Further, at least one blade sits on the mounting blade strut and is substantially parallel to the face of the mounting blade strut. A retaining means that extends through a pivot aperture of the blade where the pivot aperture is substantially perpendicular to the blade. The present invention may further include an axial cylinder that extends through the pivot aperture of the blade and into a blade attachment portal. The axial cylinder attaches to a retaining nut after the axial cylinder extends through the mounting blade strut. A retaining head of the retaining means retains the blade, holding it against the mounting blade strut. Still further, the present invention may include a drive surface located on the blade and adjacent to a pivot aperture. The present invention may further include a cutting surface that extends away from the drive surface and the pivot aperture designed to cut through the endplate of vertebrate. The invention may further include a cutting point located at the distal end of blade for puncturing the endplates, an inserter attachment portal located at the anterior face of the main body, at least one drive screw portal located at the anterior face of the main body, and one or more drive screws. When the drive screw contacts a drive surface of the blade, and when a rotational force is applied causing the blade to rotate about the retaining means.

DETAILED DESCRIPTION

Figure 1:
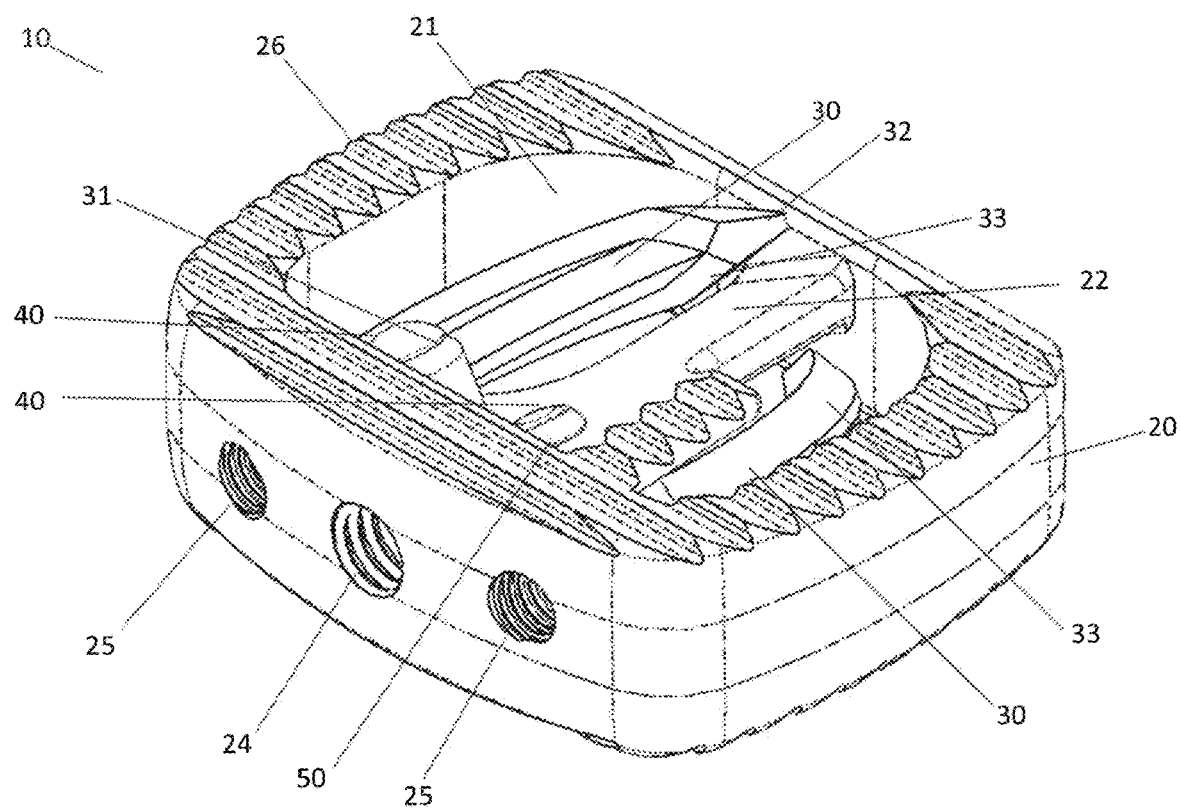
FIG. 1—Isometric View of Device with Blades inside cavity.
Figure 2:
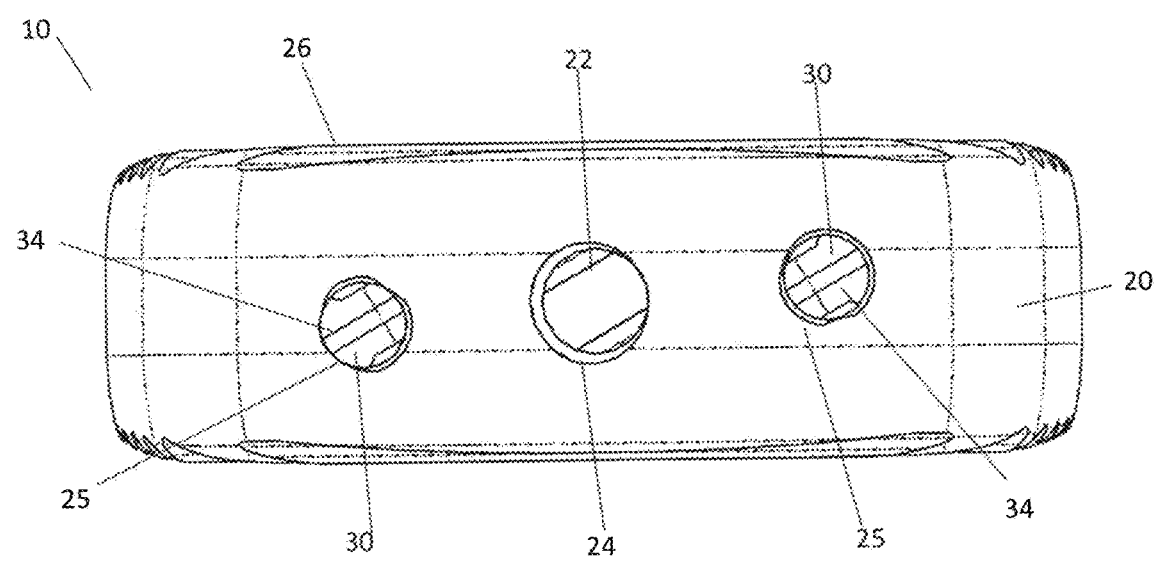
FIG. 2—Anterior View of Device with Blades inside cavity.
Figure 3:
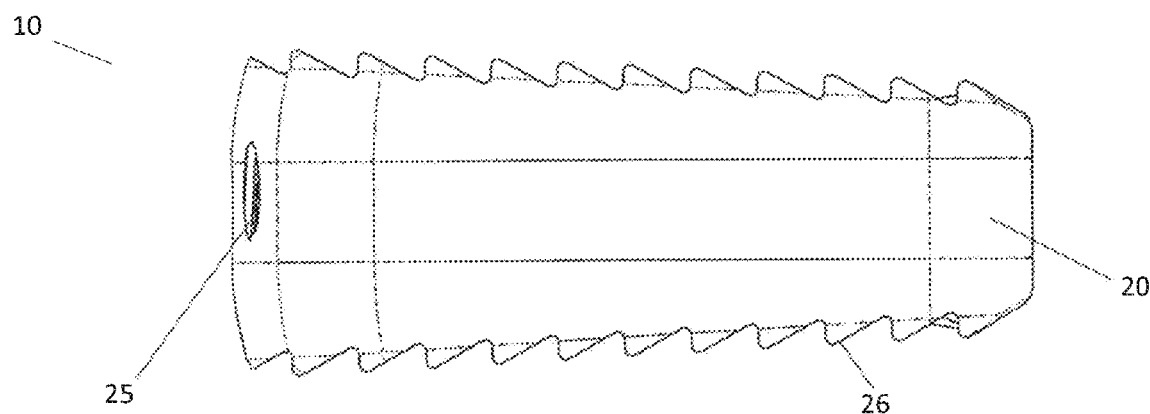
FIG. 3—Lateral View of Device with Blades inside cavity.
Figure 4:
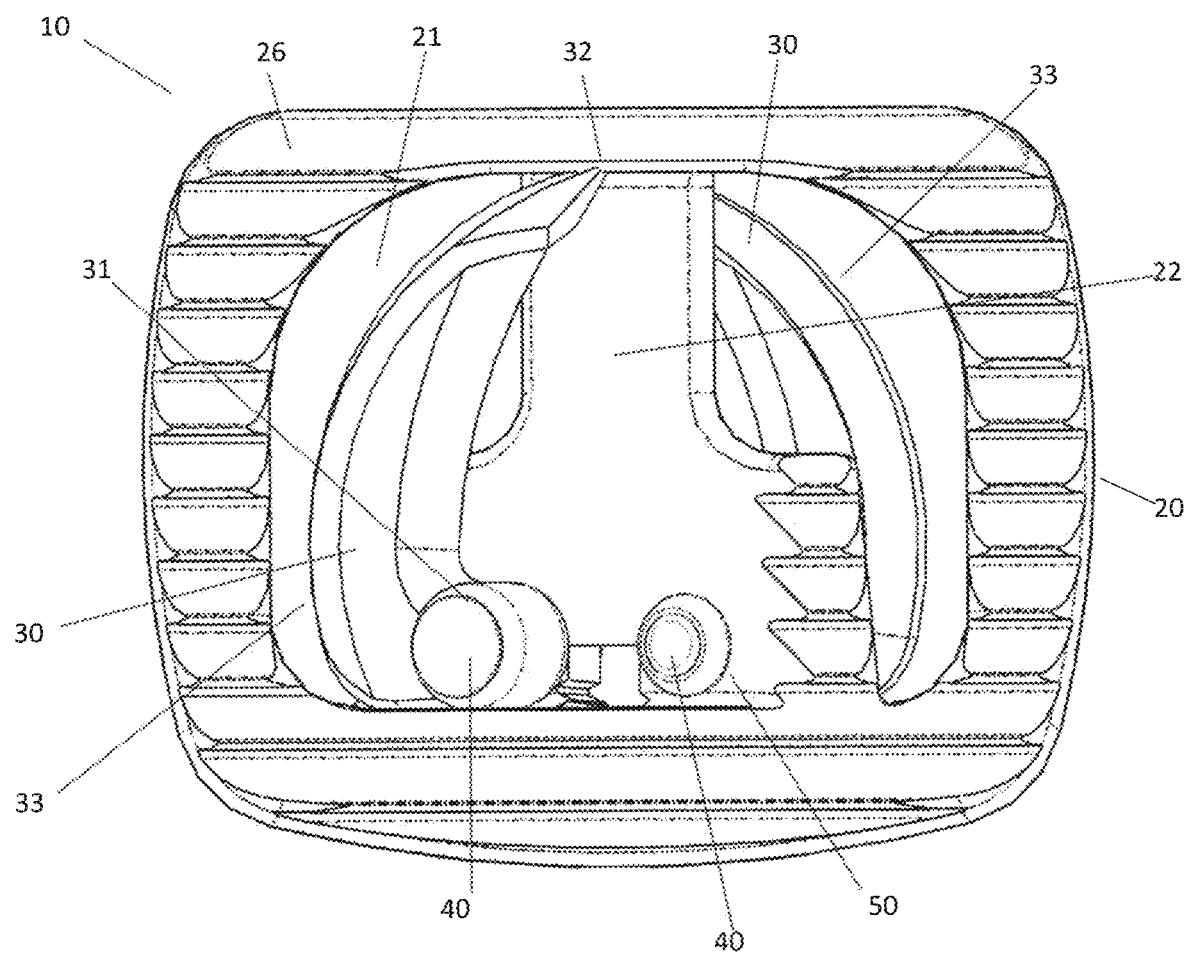
FIG. 4—Superior View of Device with Blades inside cavity.
Figure 5:
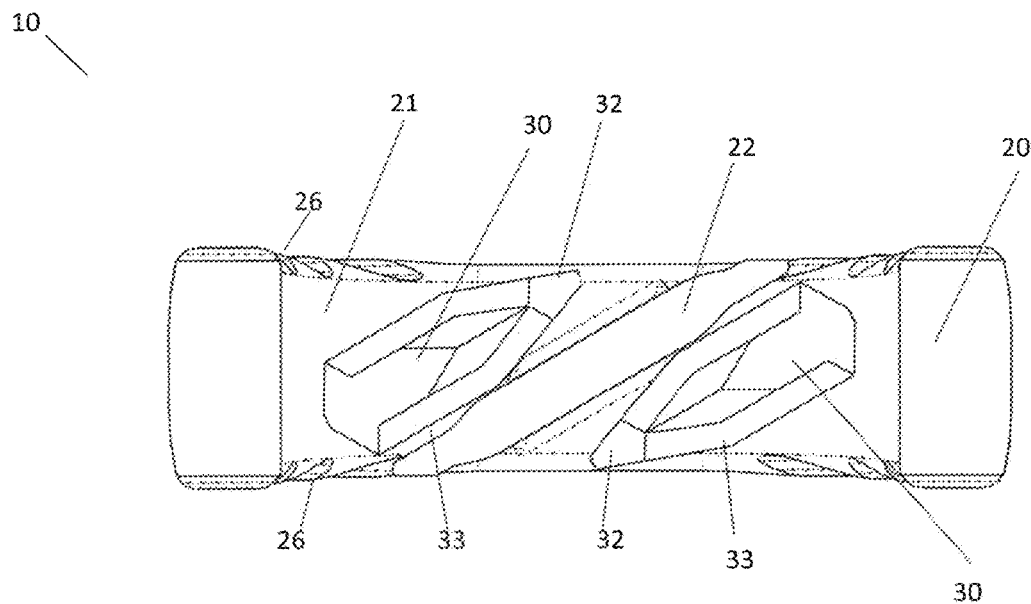
FIG. 5—Lateral Plane Cross Section View of Device with Blades inside cavity.
Figure 6:
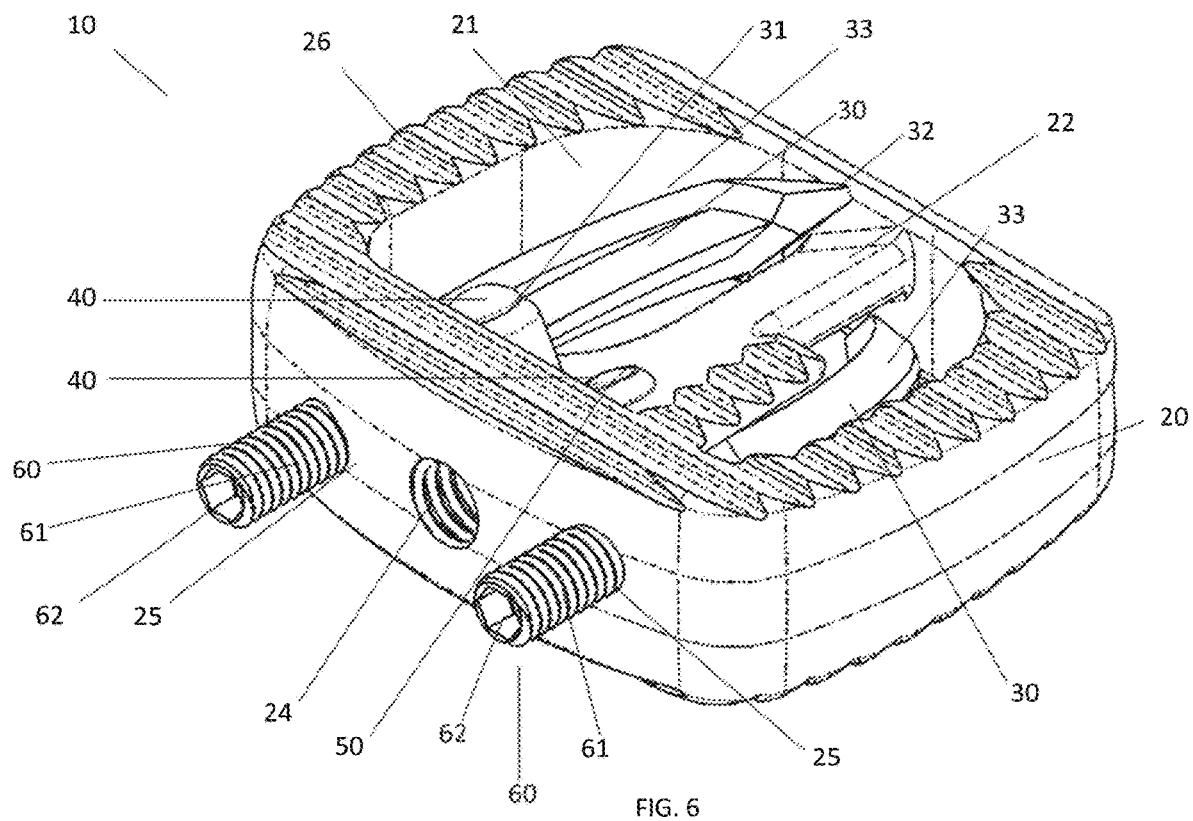
FIG. 6—Isometric View of Device with Blades inside cavity with Drive Screws Attached.
Figure 7:
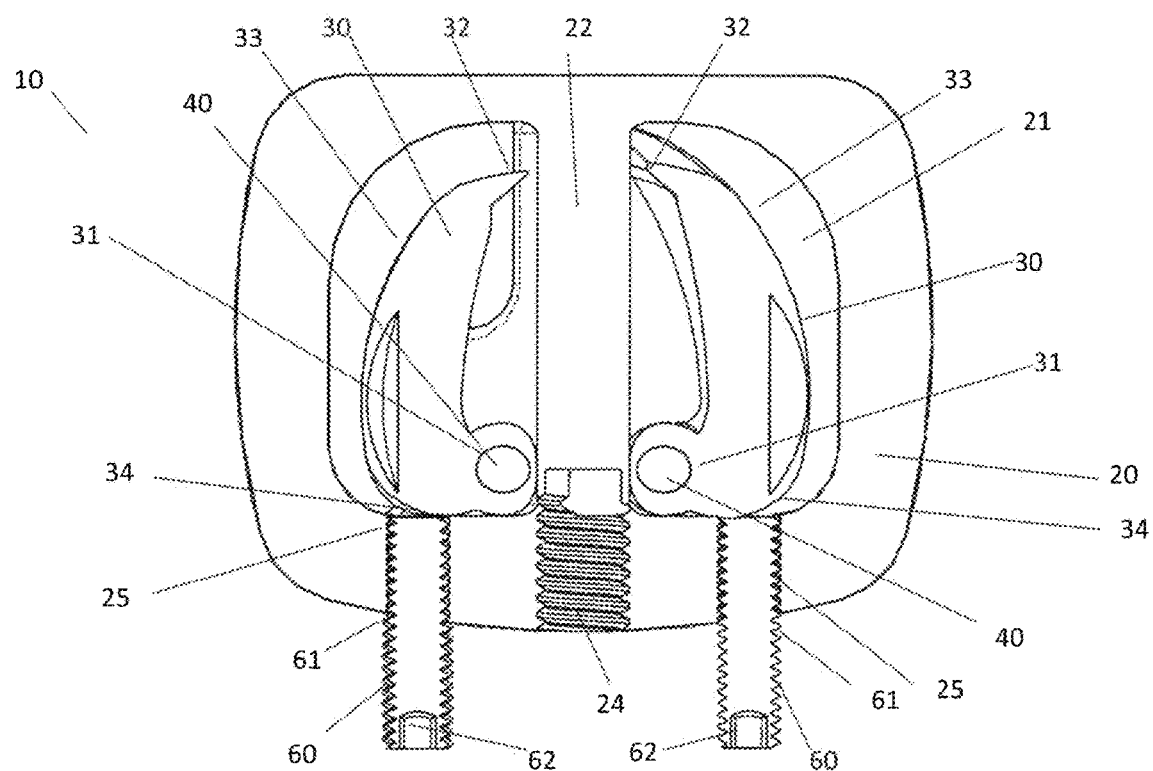
FIG. 7—Coronal Plane Cross Section of Device with Blades inside cavity with Drive Screws Attached.
Figure 8:
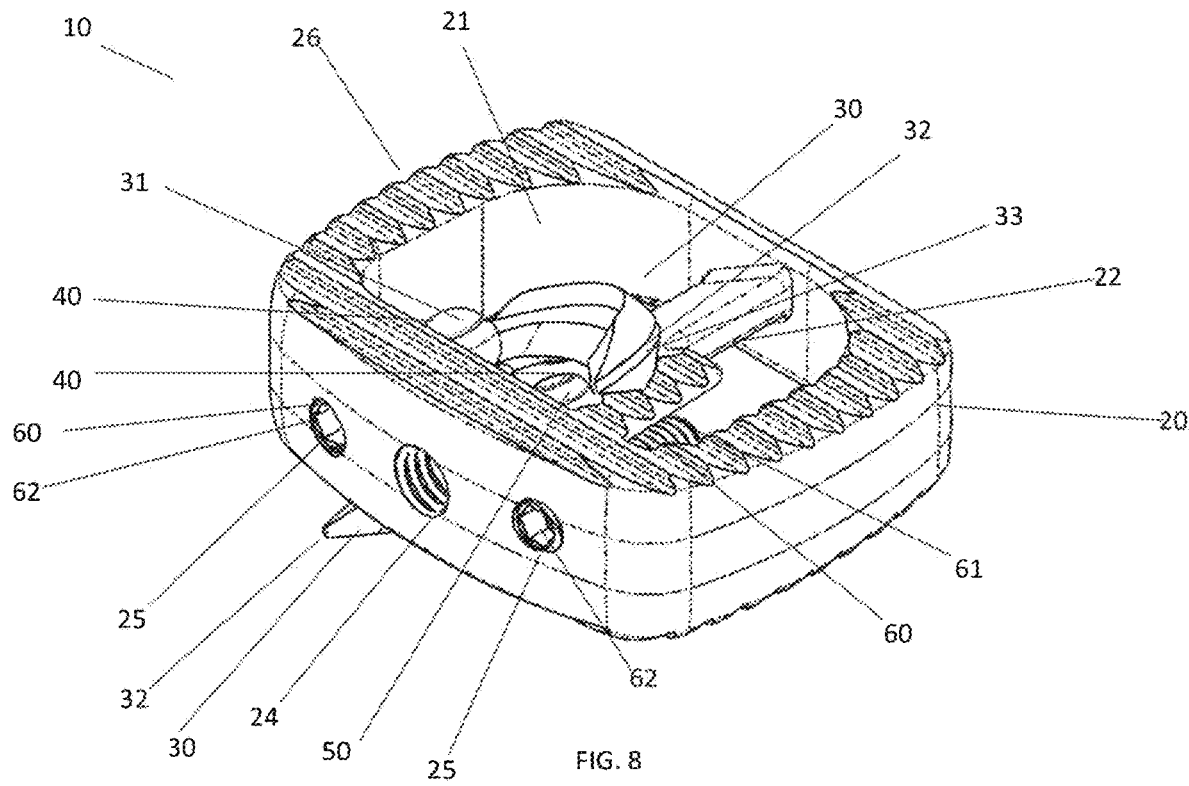
FIG. 8—Isometric View of Device with Blades deployed.
Figure 9:
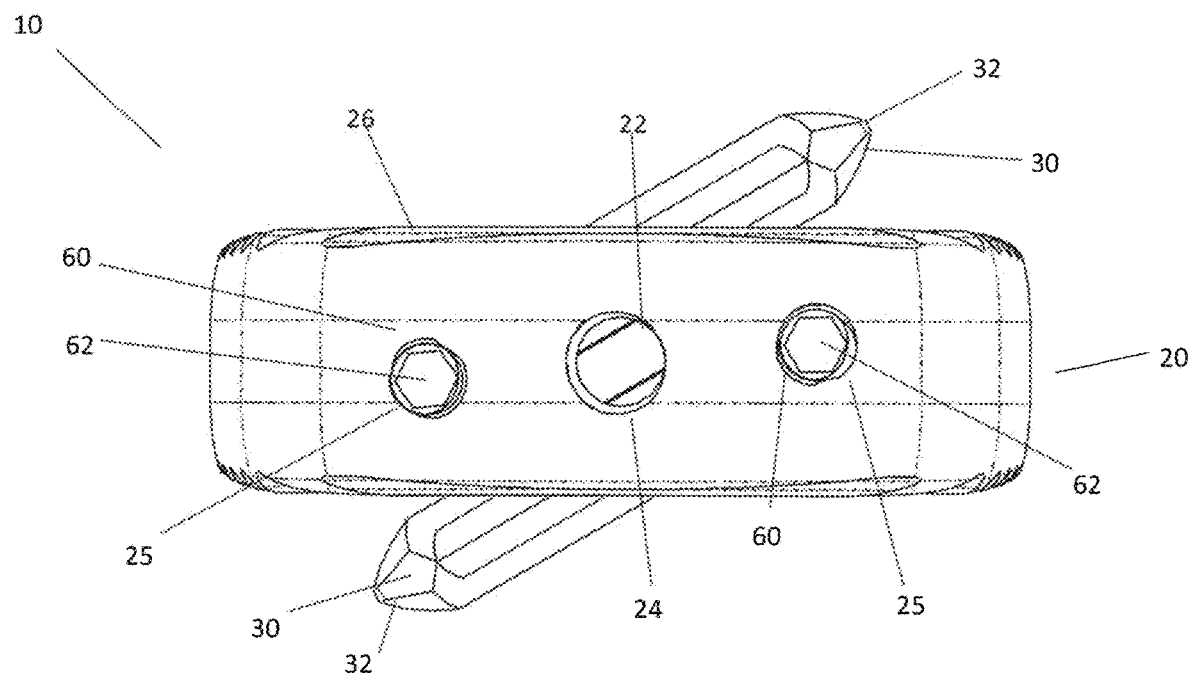
FIG. 9—Anterior View of Device with Blades Deployed.
Figure 10:
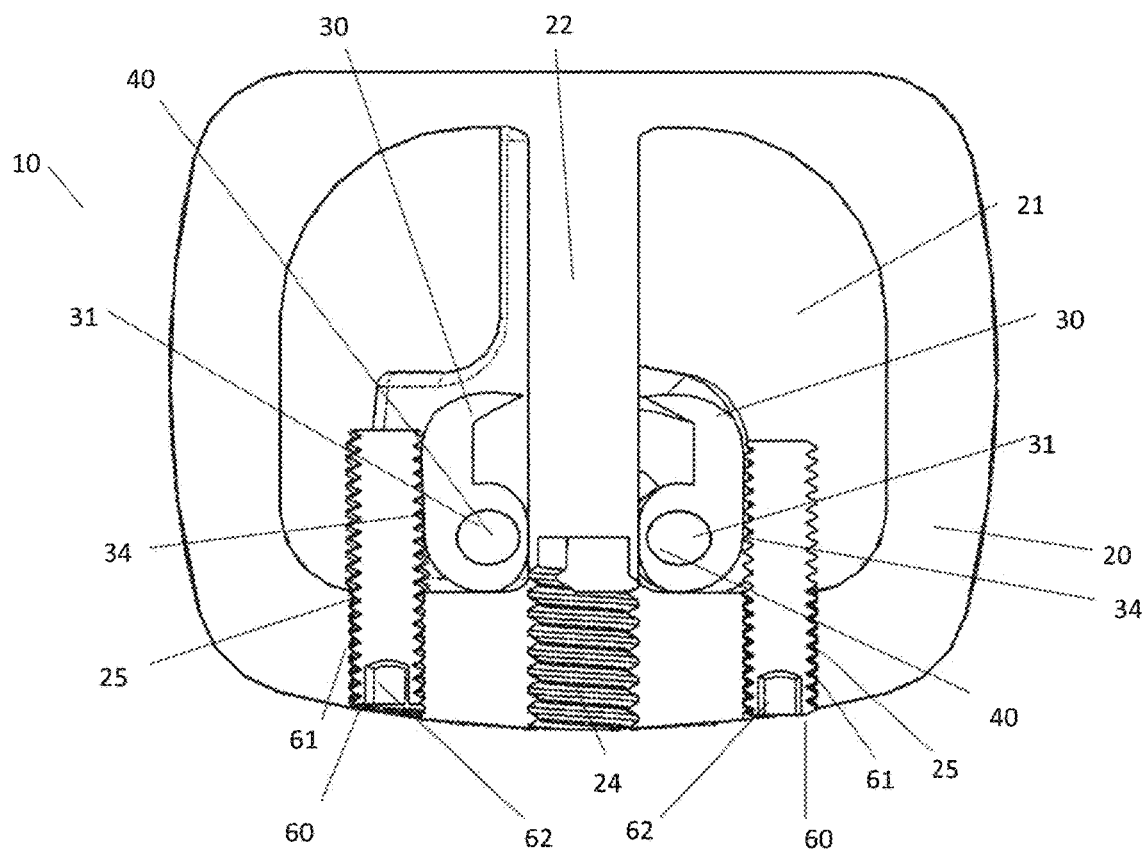
FIG. 10—Coronal Plane Cross Section of Device with Blades deployed.
Figure 11:
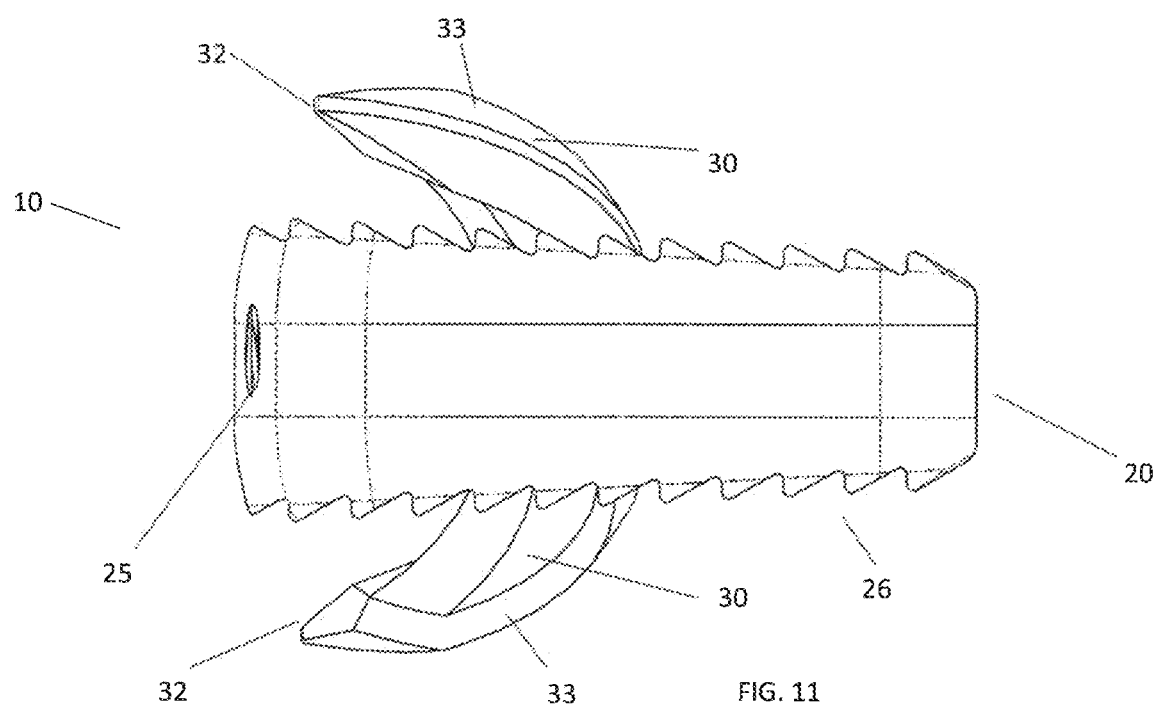
FIG. 11—Lateral View of Device with Blades Deployed.
Figure 12:
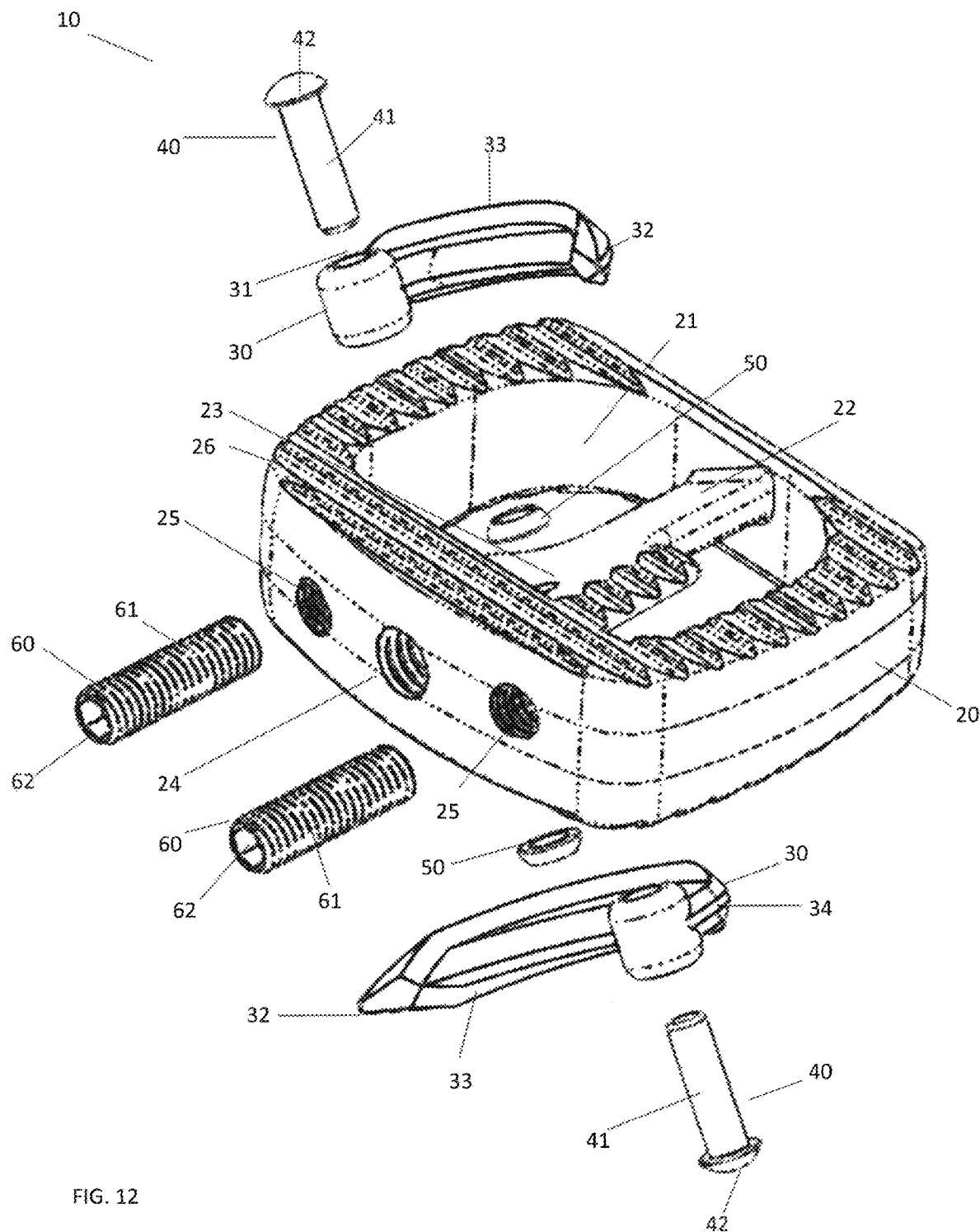
FIG. 12—Isometric Exploded View of Device.

As shown in FIGS. 1-12, the preferred embodiment interbody device 10 includes a main body 20 and at least one blade 30. Blade 30 is contained initially within central cavity 21 of main body 20 during insertion of the device 10. Once inserted into the body, blade 30 is then deployed into the endplates of the vertebrae.

Main body 20 includes a central cavity 21 which extends from the superior to inferior portions of body 20. Located within central cavity 21 is blade mounting strut 22, spanning from anterior to posterior faces of cavity 21. Blade mounting strut 22 superior and inferior faces are at an angle to superior and inferior faces of the main body 20. This angle is anywhere between 1 and 89 degrees, meaning it is neither parallel nor perpendicular. Mounting strut 22 has at least one blade attachment portal 23, which runs substantially perpendicular to the face of strut 22. There is one blade attachment portal 23 per each blade 30. Blade attachment portal 23 may be smooth or threaded.

Blade 30 sits on strut 22, being substantially parallel to the face of strut 21. Blade 30 is held to strut 22 with retaining means 40. Retaining means 40 extends through pivot aperture 31 of blade 30. Pivot aperture 31 is substantially perpendicular to blade 30. As noted by its name, blade 30 may pivot or rotate about pivot aperture 31, and therefore pivot about retaining means 40. Retaining means 40 is comprised of two features, axial cylinder 41, and retaining head 42. Axial cylinder 41 extends through pivot aperture 31 of blade 30 and into blade attachment portal 23. Axial cylinder 41 may be smooth or threaded. Axial cylinder 41 attaches to retaining nut 50 after it extends through strut 22. Retaining head 42 of retaining pin 40 retains blade 30, holding it against the strut 22. As blade 30 rotates, it does so at the same angle as strut 22.

On blade 30, adjacent to pivot aperture 31 is drive surface 34. Extending away from drive surface 34 and pivot aperture 31 is cutting surface 33. Cutting surface 33 is a blade feature designed to cut through the endplate of the vertebrate. However, cutting surface 33 of the blade is wide enough in order to hold against the bone, but also has a thickness so as to prevent it from bending. In this preferred embodiment, the cross section of blade 30 and cutting surface 33 is generally a T-shape. Also, cutting surface 33 is curved about an axis substantially parallel to the axis of pivot aperture 31. At the distal end of blade 30 is cutting point 32 for puncturing the endplates. Drive surface 34 of blade 30 is substantially perpendicular to the tangency of cutting surface 33 curvature.

The anterior face of main body 20 is defined by inserter attachment portal 24 and at least one drive screw portal 25, and one drive screw portal 25 per blade 30. Indeed, the axis of drive screw portal 25 is in line with drive surface 34 of the blade, allowing blade 30 to be viewed through portal 25. Drive screw portal 25 of main body 20 may be smooth or threaded. During insertion of device 10, portal 25 may remain empty, or may carry drive screws 60 in each.

Once device 10 is implanted into the spine, drive screws 60, defined by threads 61 and drive feature 62, are moved distally, towards blade 30 inside cavity 21 of main body 20. Drive screw 60 contacts drive surface 34 of blade 30, thereby forcing blade 30 to begin to rotate about retaining means 40. As blade 30 rotates, it rotates out of cavity 21 and contacts the vertebral endplates. Cutting point 32 being the first portion of blade 30 to make contact, puncturing the endplate. As blade 30 continues to rotate, driven by screws 60, wider cutting surface 33 slices into the vertebrae. Eventually, blade 30 rotates 90 degrees, and drive surface 34 is substantially parallel to the axis of screw 60. This prevents blade 30 from rotating backwards into cavity 21.

Once fully deployed, blade's 30 wide cutting surface 33 is substantially perpendicular to the insertion axis of device 10, thereby preventing device 10 from backing out in vivo. Retaining nut 50 serves a secondary purpose of preventing blade 30 from over rotating, thereby maintaining blade 30 in its most extended position and preventing micromotion.

It will be apparent to those skilled in the art that various modifications and variations can be made to the disclosed apparatus, system, and method. Other embodiments will be apparent to those skilled in the art from consideration of the specification and practice of the disclosed method and apparatus. It is intended that the specification and examples be considered as exemplary only, with a true scope being indicated by the following claims.

What is claimed is:

1. An interbody spinal fusion device comprising:
   a main body with a central cavity that extends from a superior portion of the main body to an inferior portion of the main body;
   a mounting blade strut attached between an anterior face and a posterior face of the central cavity, the mounting blade strut comprising,
      a superior face angled toward the superior portion of the main body, wherein the superior face is angled between 1 and 89 degrees relative to the superior portion of the main body,
      an inferior face angled toward the inferior portion of the main body, wherein the inferior face is angled between 1 and 89 degrees relative to the inferior portion of the main body,
      a first blade attachment portal formed in the superior face of the mounting blade strut, and
      a second blade attachment portal formed in the inferior face of the mounting blade strut;
   a first blade rotatably connected to the superior face of the mounting blade strut at the first blade attachment portal by a first retaining means; and
   a second blade rotatably connected to the inferior face of the mounting blade strut at the second blade attachment portal by a second retaining means, wherein the mounting blade strut separates the first blade from the second blade.

2. The interbody spinal fusion device of claim 1, wherein the first blade is movable independent of the second blade.

3. The interbody spinal fusion device of claim 1, wherein the first blade and second blade each have a cutting point at a first end, the first end being distal from where each of the blades attaches to the mounting blade strut.

4. The interbody spinal fusion device of claim 3, wherein the first blade and the second blade each have a drive surface at a second end, the second end being opposite the first end on each of the blades.

5. The interbody spinal fusion device of claim 4, wherein the first blade and the second blade each have cutting surfaces formed on one or more sides of each of the first and second blades, the cutting surfaces of each of the first blade and the second blade extending away from the respective cutting points of the first blade and the second blade.

6. The interbody spinal fusion device of claim 1, wherein the mounting blade strut is a single piece.

7. The interbody spinal fusion device of claim 1, further comprising an inserter attachment portal formed in an anterior face of the main body.

8. The interbody spinal fusion device of claim 1, further comprising one or more drive screw portals formed through an anterior face of the main body to the central cavity, wherein each of the one or more drive screw portals is aligned with either the first blade or the second blade.

9. The interbody spinal fusion device of claim 8, further comprising a drive screw received in each of the one or more drive screw portals, wherein the drive screw is drivable through the drive screw portal to push either the first or the second blade to be rotated into a deployed position.

10. An interbody spinal fusion device comprising:
    a main body with a central cavity that extends from a superior portion of the main body to an inferior portion of the main body;
    a mounting blade strut spanning from an anterior face of the central cavity to a posterior face of the central cavity, the mounting blade strut comprising,
       a superior face angled toward the superior portion of the main body,
       an inferior face angled toward the inferior portion of the main body,
       a first blade attachment portal formed in the superior face of the mounting blade strut, and
       a second blade attachment portal formed in the inferior face of the mounting blade strut;
    a first blade pivoting on the superior face of the mounting blade strut, wherein the first blade is uncovered with respect to the superior portion of the main body;
    a second blade pivoting on the inferior face of the mounting blade strut, wherein the second blade is uncovered with respect to the inferior portion of the main body;
    a first drive screw portal and a second drive screw portal, each formed through an anterior face of the main body to the central cavity, wherein the first drive screw portal is aligned with the first blade and the second drive screw portal is aligned the second blade;

a first drive screw received in the first drive screw portal, wherein the first drive screw is drivable through the first drive screw portal to push the first blade to be rotated into a deployed position; and a second drive screw received in the second drive screw portal, wherein the second drive screw is drivable through the second drive screw portal to push the second blade to be rotated into the deployed position, the first blade being rotatable independent of the second blade.

11. The interbody spinal fusion device of claim 10, wherein the superior face is angled between 1 and 89 degrees relative to the superior portion of the main body and the inferior face is angled between 1 and 89 degrees relative to the inferior portion of the main body.

12. The interbody spinal fusion device of claim 10, wherein the mounting blade strut separates the first blade from the second blade.

13. The interbody spinal fusion device of claim 10, wherein the first blade and the second blade each have a cutting point at a first end, the first end being distal from where each of the blades attaches to the mounting blade strut.

14. The interbody spinal fusion device of claim 13, wherein the first blade and the second blade each have a drive surface at a second end, the second end being opposite the first end on each of the blades.

15. The interbody spinal fusion device of claim 14, wherein the first drive screw pushes against the drive surface of the first blade to push and rotate the first blade into the deployed position and the second drive screw pushes against the drive surface of the second blade to push and rotate the second blade into the deployed position.

16. An interbody spinal fusion device comprising:
a main body with a central cavity that extends from a superior portion of the main body to an inferior portion of the main body;

a mounting blade strut spanning from an anterior face of the central cavity to a posterior face of the central cavity, the mounting blade strut comprising,
 a superior face angled toward the superior portion of the main body,
 an inferior face angled toward the inferior portion of the main body,
 a first blade attachment portal formed in the superior face of the mounting blade strut, and
 a second blade attachment portal formed in the inferior face of the mounting blade strut;

a first blade pivoting on the superior face of the mounting blade strut, wherein the first blade is uncovered with respect to the superior portion of the main body;

a second blade pivoting on the inferior face of the mounting blade strut, wherein the second blade is uncovered with respect to the inferior portion of the main body and the mounting blade strut separates the first blade from the second blade;

a first drive screw portal and a second drive screw portal, each formed through the anterior face of the main body to the central cavity, wherein the first drive screw portal is aligned with the first blade and the second drive screw portal is aligned the second blade.

17. The interbody spinal fusion device of claim 16, further comprising a drive screw received in each of the drive screw portals, wherein the drive screw is drivable through the drive screw portal to push either the first or the second blade to be rotated into a deployed position and the first blade is movable independent of the second blade.

18. The interbody spinal fusion device of claim 16, wherein the first blade is connected to the mounting blade strut at a first blade attachment portal and the second blade is connected to the mounting blade strut at a second blade attachment portal.

19. The interbody spinal fusion device of claim 18, wherein the first and second blade attachment portals are on opposite lateral sides of the mounting blade strut.

* * * * *